(12) United States Patent
Kim et al.

(10) Patent No.: US 11,154,362 B2
(45) Date of Patent: Oct. 26, 2021

(54) CUSTOMIZED SURGICAL GUIDE AND CUSTOMIZED SURGICAL GUIDE GENERATING METHOD AND GENERATING PROGRAM

(71) Applicants: THE ASAN FOUNDATION, Seoul (KR); UNIVERSITY OF ULSAN FOUNDATION FOR INDUSTRY COOPERATION, Ulsan (KR)

(72) Inventors: Namkug Kim, Seoul (KR); Guk Bae Kim, Seoul (KR); Beom Seok Ko, Seoul (KR); Sang Wook Lee, Seoul (KR); Sei Hyun Ahn, Seoul (KR); Byung Ho Son, Seoul (KR); Jong Won Lee, Seoul (KR)

(73) Assignees: THE ASAN FOUNDATION, Seoul (KR); UNIVERSITY OF ULSAN FOUNDATION FOR INDUSTRY COOPERATION, Ulsan (KR)

(\*) Notice: Subject to any disclaimer, the term of this patent is extended or adjusted under 35 U.S.C. 154(b) by 175 days.

(21) Appl. No.: 16/414,422

(22) Filed: May 16, 2019

(65) Prior Publication Data
US 2019/0269460 A1 Sep. 5, 2019

Related U.S. Application Data

(63) Continuation of application No. PCT/KR2017/012906, filed on Nov. 15, 2017.

(30) Foreign Application Priority Data

Nov. 16, 2016 (KR) .................. 10-2016-0152885

(51) Int. Cl.
*A61B 34/10* (2016.01)
*A61B 17/15* (2006.01)
(Continued)

(52) U.S. Cl.
CPC .............. *A61B 34/10* (2016.02); *A61B 17/15* (2013.01); *A61B 17/17* (2013.01);
(Continued)

(58) Field of Classification Search
CPC ...... A61B 17/17; A61B 17/3403; A61B 34/10
See application file for complete search history.

(56) References Cited

U.S. PATENT DOCUMENTS 5,031,634 A * 7/1991 Simon ................ A61B 17/3403
600/567
6,122,542 A 9/2000 Lee et al.
(Continued)

FOREIGN PATENT DOCUMENTS

CN 105963002 A 9/2016
JP 2006-501904 A 1/2006
(Continued)

OTHER PUBLICATIONS

International Search Report issued in PCT/KR2017/012906; dated Feb. 14, 2018.
(Continued)

*Primary Examiner* — Zade Coley
(74) *Attorney, Agent, or Firm* — Studebaker & Brackett PC

(57) ABSTRACT

The present invention relates to a customized surgical guide device and a customized surgical guide generating method and program. A customized surgical guide generating method comprises the steps of: acquiring body surface data and treatment area data from medical image data by a computer; a first shape data generating step, wherein the first shape data is data which corresponds to the shape of the body part cover; a target point setting step of setting one or more target points; setting individual first points on the body surface accessible to the target point with a medical tool;
(Continued)

setting a guide tube length on the basis of a distance from the first point to the target point; and generating final shape data in which one or more guide tubes are combined to the first shape data by applying the guide tube length to the first point.

18 Claims, 5 Drawing Sheets

(51) Int. Cl.
  *A61B 17/17* (2006.01)
  *A61B 90/17* (2016.01)
  *A61B 17/34* (2006.01)
  *A61B 90/00* (2016.01)
  *A61B 17/00* (2006.01)
(52) U.S. Cl.
  CPC .......... *A61B 17/3403* (2013.01); *A61B 90/17* (2016.02); *A61B 2017/008* (2013.01); *A61B 2017/00526* (2013.01); *A61B 2017/3407* (2013.01); *A61B 2034/105* (2016.02); *A61B 2034/108* (2016.02); *A61B 2090/034* (2016.02); *A61B 2090/395* (2016.02); *A61B 2090/3933* (2016.02)

(56) References Cited

U.S. PATENT DOCUMENTS

| | | | | |
|---|---|---|---|---|
| 2004/0133124 | A1* | 7/2004 | Bates | A61B 10/0275 600/564 |
| 2008/0171934 | A1* | 7/2008 | Greenan | A61B 5/06 600/411 |
| 2013/0218163 | A1* | 8/2013 | Frey | A61B 34/10 606/87 |
| 2013/0274778 | A1* | 10/2013 | Mercier | A61B 90/11 606/172 |
| 2014/0039451 | A1* | 2/2014 | Bangera | G05B 19/4099 604/506 |
| 2016/0038252 | A1 | 2/2016 | Barth, Jr. et al. | |

FOREIGN PATENT DOCUMENTS

| | | |
|---|---|---|
| JP | 2012-019964 A | 2/2012 |
| KR | 10-2013-0137157 A | 12/2013 |
| KR | 10-2015-0003275 A | 1/2015 |
| WO | 2013/130529 A1 | 9/2013 |
| WO | WO-2016007717 A1 * 1/2016 ............. A61B 90/11 |

OTHER PUBLICATIONS

The extended European search report issued by the European Patent Office dated Aug. 28, 2019, which corresponds to European Patent Application No. 17870686.7-1113 and is related to U.S. Appl. No. 16/414,422.

An Office Action; "Notice of Reasons for Refusal", mailed by the Japanese Patent Office dated Mar. 10, 2020, which corresponds to Japanese Patent Application No. 2019-526302 and is related to U.S. Appl. No. 16/414,422; with English language translation.

* cited by examiner

CUSTOMIZED SURGICAL GUIDE AND CUSTOMIZED SURGICAL GUIDE GENERATING METHOD AND GENERATING PROGRAM

CROSS-REFERENCE TO RELATED APPLICATIONS

The present application is a continuation of International Patent Application No. PCT/KR2017/012906, filed Nov. 15, 2017, which is based upon and claims the benefit of priority to Korean Patent Application No. 10-2016-0152885, filed on Nov. 16, 2016. The disclosures of the above-listed applications are hereby incorporated by reference herein in their entirety.

BACKGROUND

Embodiments of the inventive concept described herein relate to a customized surgical guide, and a customized surgical guide producing method, and a producing program, and more particularly, to a customized surgical guide, a customized surgical guide producing method, and a producing program by which surgery is performed in accordance with a state of a treatment target region of a specific patient during the specific patient's surgery.

In surgery, medical staffs measure a region to be subjected to surgery based on medical images. In this process, the region measurement is dependent on the surgeon's eye-based measurement and experience. Thus, it may happen that a region to be removed is not completely removed. Further, a region to be removed is not accurately measured such that a large region than the region to be removed is cut off.

Further, a removal area on a skin surface is marked before surgery is performed. However, when the surgery starts and the body portion is excised, a marker on the surface of the skin may not match an inner portion to be removed, such that an accuracy at which the scope of surgery within the body portion is determined is lowered. In order to mark a certain point inside the body, an ultrasonic or mammography guide H-wire is inserted to remove a corresponding body portion. This may have marking inaccuracy. Further, this takes pain and long surgery time. Occasionally, a part of the H-wire is cut off or left in the body during surgery.

SUMMARY

Embodiments of the inventive concept provide a customized surgical guide, and a customized surgical guide producing method, and a producing program by which a removal region in a body portion subjected to surgery is three-dimensionally displayed, and, thus, accurate visual identification of the removal region (i.e., treatment target region) is realized during the surgery of the removal region.

Further, embodiments of the inventive concept provide a customized surgical guide produced based on a treatment plan that allows a medical instrument to reach a plurality of target points within a body portion for treatment of the treatment target region at a minimal treatment procedure, and a customized surgical guide producing method, and a producing program.

The purposes to be achieved by the inventive concept are not limited to the purposes mentioned above, and other purposes not mentioned may be clearly understood by those skilled in the art from the following descriptions.

According to an exemplary embodiment, a customized surgical guide includes at least one guide tube through which a medical instrument is insertable; and a body portion cover covering a surface of a specific body portion, wherein the body portion cover is coupled to the at least one guide tube. The body portion cover has a hole defined therein through which the medical instrument passes. The medical instrument passes through the guide tube and then through the hole toward the body portion. The body portion cover is shaped to conform to a surface of the body portion of a patient. The body portion cover defines a position of the guide tube such that the medical instrument reaches a target point within the body portion. The guide tube has a larger inner diameter than an outer diameter of the medical instrument. The guide tube has a length sized such that an insertable depth of the medical instrument into the body is limited to a set depth from a first point to the target point. The first point is present on the surface of the body portion, and the guide tube is coupled to the body portion cover at a position thereof corresponding to the first point. The target point is present on a surface of or inside a treatment target region, or is spaced by a specific distance from the treatment target region.

According to the inventive concept as defined above, following various effects may be realized.

First, using the customized surgical guide that assists in performing patient-customized surgery may allow optimal surgery for the patient. For example, when a to-be-removed lesion (for example, tumor) within the affected portion should be removed, the patient-customized surgical guide is used to produce at least one dye column in the body portion. The dye column may be used to allow the medical staff to visually check the to-be-removed region during surgery. Thus, the medical staff may remove a minimal tissue via two-or three-dimensional marking using the dye column.

Second, since the guide tube is produced by calculating a depth to the target point based on the medical image data, the medical staff may perform the surgery without paying attention to the depth of insertion of the medical instrument, (for example, syringe). In other words, when the medical instrument is fully inserted into the guide tube of the customized surgery guide, the medical instrument reaches the target point, so that the surgery can be easily performed.

Third, the body portion cover is shaped to conform to the body portion shape, and the body portion cover defines a position of the guide tube such that the medical instrument accurately reaches the target point within the body portion. This prevents treatment from being performed on a wrong target point or prevents erroneously marking in the body portion.

Fourth, even when there is a difference between a posture of the patient at which the medical image data is obtained and a posture of the patient at which the surgery is performed, the customized surgical guide may allow the medical instrument to accurately reach the target point.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
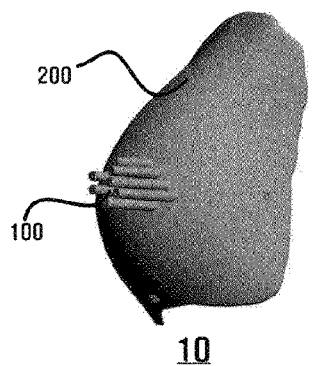
FIG. 1 is a perspective view of a customized surgical guide according to one embodiment of the inventive concept.

A customized surgical guide according to one embodiment of the inventive concept includes at least one guide tube through which a medical instrument is insertable; and a body portion cover covering a surface of a specific body portion. The body portion cover is coupled to the at least one guide tube. The body portion cover has a hole defined therein through which the medical instrument passes. The medical instrument passes through the guide tube and then through the hole toward the body portion. The body portion cover is shaped to conform to a surface of the body portion of a patient. The body portion cover defines a position of the guide tube such that the medical instrument reaches a target point within the body portion. The guide tube has a larger inner diameter than an outer diameter of the medical instrument. The guide tube has a length sized such that an insertable depth of the medical instrument into the body is limited to a set depth from a first point to the target point. The first point is present on the surface of the body portion, at which the guide tube is located. The target point is present on a surface of or inside a treatment target region, or is spaced by a specific distance from the treatment target region.

Further, when the medical instrument is a syringe with a specific needle length, the guide tube may be formed so that the syringe needle reaches the target point, and the target point may be a specific point on a surface of the treatment target region in the body portion. While the syringe is removed away from the target point through the guide tube, the syringe may supply dye to form a dye column in the body portion.

Further, when the medical instrument performs treatment on a treatment range defined as a specific range from a specific point which the inserted medical instrument reaches, the target point may be at least one specific point located within the treatment target region, and the at least one specific point may define at least one treatment range covering the treatment target region. A number of the guide tubes may be equal to a number of the target points, and each guide tube may be formed on the first point of the body portion cover and extends in a direction from the first point toward each target point.

Further, the body portion cover may be formed to conform to body surface acquired based on medical image data. The guide tube may have a length set based on a distance on the medical image data from the first point on the body surface to the target point that the medical instrument should reach.

Further, the customized surgical guide may be made of deformable material and may be inserted using a laparoscope into the body and then be placed on the body portion surface.

Further, when the body portion including the treatment target region has a shape varying according to a posture of the patient, the body portion cover may cover the body portion and may fix a shape of the body portion into a specific shape.

Further, when a distal end of the medical instrument reaches the target point, the guide tube may be fitted with the medical instrument.

A method of producing a customized surgical guide according to another embodiment of the inventive concept, the guide including a guide tube through which a medical instrument is inserted, and a body portion cover contacting a body surface, includes acquiring, by a computer, body surface data and treatment region data from medical image data; generating, by the computer, first shape data based on the body surface data, the first shape data defining a shape of the body portion cover; setting, by the computer, at least one target point, the target point being present on a surface of or inside a treatment target region; setting, by the computer, each first point on the body surface from which the medical instrument is accessible to the target point; setting, by the computer, a length of the guide tube based on a distance from the first point to the target point; and applying, by the computer, the guide tube length to the first point to generate last shape data as a combination between the first shape data and shape data of at least one guide tube.

Further, when the medical instrument is a syringe with a specific needle length, the target point may be a specific point on a surface of the treatment target region in the body portion. While the syringe may be removed away from the target point through the guide tube, the syringe may supply dye to form a dye column in the body portion.

Further, when the medical instrument performs treatment on a treatment range defined as a specific range from a specific point which the inserted medical instrument reaches, the target point may be at least one specific point located within the treatment target region. The setting of the at least one target point may include setting at least one target point to define at least one treatment range covering the treatment target region.

Further, the generating of the first shape data may include: obtaining entire shape data of the body portion; and generating shape data of the body portion cover covering a specific body portion based on the entire shape data. The body portion cover may cover the body portion and fixes a shape of the body portion into a specific shape.

Further, when a first posture of a patient at which the medical image data is taken and a second posture of the patient at which surgery is performed are different, the method may further include calculating a positional change of the treatment target region when a posture of the patient changes from the first posture to the second posture. The setting of the at least one target point, the setting of each first point, and the setting of the length of the guide tube may be performed based on the changed position of the treatment target region.

Further, the setting of the first point may include setting the first point from which the medical instrument reaches the target point without passing through the treatment target region.

Further, when the medical instrument is curved at a specific curvature, the setting of the first point may include setting the first point from which the medical instrument reaches the target point while moving along a curved path having the specific curvature within the body. The generating of the last shape data may include generating curvature data of the guide tube equal to the curvature of the medical instrument.

A customized surgical guide producing program according to still another embodiment of the inventive concept may be stored in a medium for carrying out the customized surgical guide producing method in combination with a computer as hardware.

Hereinafter, preferred embodiments of the inventive concept will be described in detail with reference to the accompanying drawings. Advantages and features of the inventive concept, and methods of accomplishing the same, will become apparent with reference to the embodiments described in detail below with reference to the accompanying drawings. However, the inventive concept is not limited to the embodiments disclosed below, but may be embodied in various forms. These embodiments are provided so that the disclosure of the inventive concept is complete and that it is believed that the disclosure is intended to be completely understood by those skilled in the art to which the inventive concept belongs. The inventive concept is only defined by the scope of the claim. Like reference numerals refer to like elements throughout the specification.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

As used herein, a term "computer" includes all of various devices that can perform computational processing and present the results visually to the user. For example, the computer may include a desktop PC, a notebook, a smartphone, a tablet PC, a cellular phone, a PCS phone (Personal Communication Service phone), synchronous/asynchronous IMT-2000 (International Mobile Telecommunication-2000) mobile terminal, a palm personal computer, personal digital assistant (PDA), and so on. Further, a computer may be a medical device that acquires or observes an angiographic image.

As used herein, a term "medical image data" means image data obtained by medical imaging devices such as Computed Tomography (CT) device, MRI (Magnetic Resonance Imaging) device or the like.

As used herein, a term "treatment target region" refers to a region to be treated within a specific body portion. For example, in patients with breast cancer, the treatment target region corresponds to a tumor region in the breast as the body portion. The treatment target region may coincide with an affected region or may be actually larger than the affected region with considering an error range.

As used herein, a term "medical instrument" refers to a tool which is used for surgery, treatment, or examination, and is inserted or invaded into the body. For example, the medical instrument may be a syringe with a needle of a specific length. Further, for example, the medical instrument may be a device that is inserted into a specific body portion and applies electrical stimulation to a specific range.

As used herein, a term "target point" refers to a point reached by the medical instrument inserted through a customized surgical guide. In other words, the target point means a point of maximum depth reached by the medical instrument while movement of the medical instrument is limited by the guide tube. The target point may be a point located on the surface of or interior in the treatment target region, or a point separated by a certain distance from the treatment target region.

As used herein, a term "first point" refers to a point on the body portion surface from which the medical instrument is inserted to reach the target point. That is, the first point refers to the point on the body portion surface where the guide tube is placed when placing a customized surgical guide in the body portion.

Hereinafter, a customized surgical guide, a customized surgical guide producing method and a producing program according to embodiments of the inventive concept will be described in detail.

FIG. 1 is an illustration of a customized surgical guide 10 according to one embodiment of the inventive concept.

Referring to FIG. 1, the customized surgical guide 10 according to one embodiment of the inventive concept includes a guide tube 100 and a body portion cover 200.

The guide tube 100 refers to a tube into which a medical instrument can be inserted. The guide tube 100 has a larger diameter than that of a portion of the medical instrument that is inserted into the body. Since the portion of the medical instrument is inserted into the body, it may be dangerous when the portion of the medical instrument contacts a wall surface of the guide tube 100 and thus foreign matter is attached to the portion of the medical instrument. Therefore, the guide tube 100 has a larger diameter than that of the portion of the medical instrument such that the portion of the medical instrument is not in contact with the wall surface of the guide tube 100. For example, when the medical instrument is a syringe with a needle, the guide tube 100 has a larger diameter than that of the needle, and supports the syringe body and is oriented to an orientation of the syringe body such that the needle is inserted at an accurate angle. The guide tube 100 is formed with a length that limits a depth at which the medical instrument can be inserted into the body to a set depth from the first point to a target point 40. For example, when the medical instrument is a syringe with a needle, the guide tube 100 is formed such that the needle is inserted into the guide tube 100 and then the syringe is stopped by the guide tube 100 so that the needle enters the body only at a certain depth. For example, when the length of the needle is A, and the length of the guide tube 100 is B, the needle enters the body only as long as a length corresponding to "A-B" as the syringe is stopped by the guide tube 100. Thus, the guide tube 100 of the customized surgical guide 10 limits the depth at which the medical instrument is inserted into the body.

The length of the guide tube 100 is set based on a distance from the first point on the body surface to the target point 40 which the medical instrument should reach, on the medical image data. In one embodiment, when the customized surgical guide 10 is injected by a 3D printer, the computer analyzes a CT image or MRI image to calculate the distance from the specific first point on the surface of the body portion to the specific target point 40. Thereafter, the length of the guide tube 100 is calculated by subtracting the calculated distance from the length (for example, the length of the syringe needle) of the medical instrument used during the surgery. This allows the computer to set the length of the guide tube 100 of the customized surgical guide 10 based on the patient's treatment target region 20.

The customized surgical guide 10 according to one embodiment of the inventive concept has a number of guide tubes 100 corresponding to the number of target points 40 in the body. Since each guide tube 100 is produced to have a length and direction to reach from the first point to the target point 40, the number of the guide tubes 100 as produced may correspond to the number of the target points 40.

The body portion cover 200 is coupled to at least one guide tube 100, as in FIG. 1. That is, the body portion cover 200 has a hole defined therein through which the medical instrument inserted through the guide tube 100 passes toward the body portion. In this way, the medical instrument inserted through the guide tube 100 is invaded or inserted into the body portion along an extension of the guide tube 100.

The body portion cover 200 covers a surface of a specific body portion. Specifically, the body portion cover 200 is formed to conform to the surface of the body portion of the patient. In one embodiment, the body portion cover 200 is produced based on body surface data obtained based on the medical image data. For example, when the body portion cover 200 is injected using a 3D printer and the breast of a breast cancer patient is set as a body portion, shape data of the body portion cover 200 conforming to a surface of the patient's breast shape in capturing the MRI image or CT image is produced based on the MRI image or the CT image. Thus, the body portion cover 200 conforms to the body portion surface. Thus, when the medical instrument is inserted into the guide tube 100 of the customized surgical guide 10 produced based on the medical image data, the medical instrument reaches the target point 40 in the body portion accurately. That is, the body portion cover 200 allows the guide tube 100 to be positioned at the first point set in a treatment planning process based on the medical image data.

Figure 2:
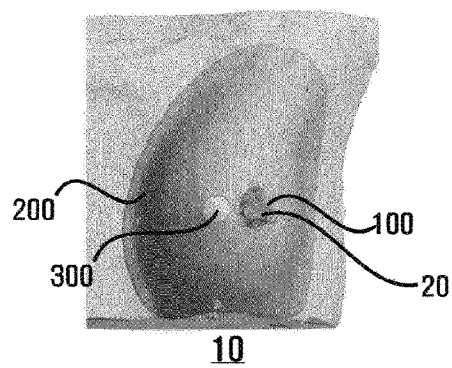
FIG. 2 is an illustration of a customized surgical guide attached to a body portion according to one embodiment of the inventive concept.

Further, in another embodiment, the customized surgical guide 10 includes a reference point 300 for precise positioning of the customized surgical guide 10 when applied to the patient, as shown in FIG. 2. The reference point 300 corresponds to a specific location of the body portion to allow the customized surgical guide 10 to be placed at the exact location set in the surgery planning or modeling. For example, when the body portion is a breast, the customized surgical guide 10 has a hole with the same size as a nipple at a point corresponding to the nipple. Thus, the accurate attachment position is set on the body portion surface while the nipple is set as the reference point 300.

In yet another embodiment, when a body portion including the treatment target region 20 has a shape changing depending on a posture of the patient, the body portion cover 200 of the customized surgical guide 10 covers the body portion and fixes the body portion into a specific shape. For example, when the body portion is the breast, a shape of the breast may change depending on a posture of the patient. Therefore, when the breast has the same shape at the breast shape in setting the target point 40 based on the medical image data, the medical instrument can reach the target point 40 through the customized surgical guide 10 accurately. Accordingly, the body portion cover 200 may be formed to cover the entire body portion, and thus to deform and retain the body portion into and as a shape obtained at imaging of the medical image data. For example, when the body portion is a breast, the body portion cover 200 may be made in the same shape as a brassiere, and may be worn on the patient during breast cancer surgery.

The customized surgical guide 10 according to one embodiment of the inventive concept may be implemented in various forms according to use purposes and may be used in various ways. In one embodiment, when the medical instrument is a syringe with a specific needle length, the guide tube 100 is formed such that the syringe needle reaches the target point 40. In this connection, the target point 40 is the specific point on the surface of the treatment target region 20 in the body portion. That is, the customized surgical guide 10 is formed such that the specific point on a surface of the treatment target region 20 (the specific point on an interface between the treatment target region 20 and a normal region) is the target point 40. The plurality of target points 40 may be indicated as points on a plane corresponding to the interface between the treatment target region 20 and normal region or may be indicated as a plurality of points on the three-dimensional space of the treatment target region 20 having a three-dimensional shape.

Figure 3:
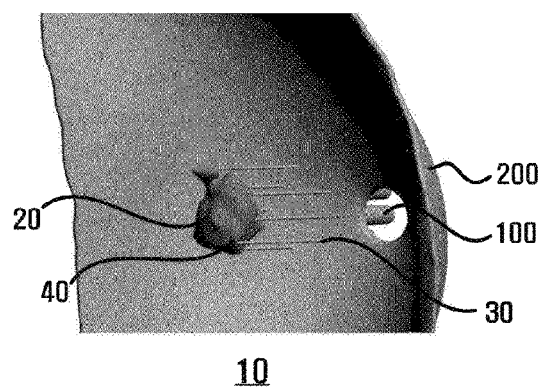
FIG. 3 is an illustration of forming a dye column from a target point of a treatment target region surface through a guide tube according to one embodiment of the inventive concept.

Specifically, as shown in FIG. 3, a syringe filled with a dye is inserted through the customized surgical guide 10 to a distal end thereof to reach the target point 40. While the syringe is removed out of the guide, the dye is slightly discharged from the syringe to dye an inside of the body portion. Thus, a dye column 30 is formed to extend from the target point 40 in the body portion to the first point of the body portion surface.

Forming a plurality of dye columns 30 through each guide tube 100 of the customized surgical guide 10 may allow an accurate to-be-removed region (that is, treatment target region 20) to be grasped. Even when the medical team cuts away the affected portion, the dye column 30 is continuously present from the target point 40. Thus, the point corresponding to the boundary of the treatment target region 20 may be confirmed in the surgical procedure.

Further, in another embodiment, when the medical instrument is of a tool for performing treatment while setting, as a treatment range, a specific range from a specific point which the medical instrument reaches, the target point 40 is at least one specific point located within the treatment target region 20 to form at least one treatment range that encompasses the treatment target region 20. That is, the target point 40 reached by the medical instrument through the guide tube 100 becomes a specific point within the treatment target region 20, while the medical instrument treats the treatment range centered on the target point 40 by providing electricity thereto.

In this connection, the number of the guide tubes 100 corresponds to the number of the target points 40. Each of the number of the guide tubes 100 is formed on the first point of the body portion cover 200 and extends in a direction from the first point toward the target point 40. When the treatment target region 20 is larger than the treatment range, the customized surgical guide 10 includes a specific number of guide tubes 100 such that treatment ranges formed around target points 40 of the guide tubes 100 respectively may overlap to cover the treatment target region 20. Thus, the surgeon can perform the surgery simply by inserting the medical instrument(s) into the guide tubes 100 which respectively guide the medical instrument to the target points 40 set according to the patient surgery plan.

Further, in another embodiment, the customized surgical guide 10 is formed of a deformable material, and is inserted using a laparoscope into the body, and then placed on the body portion surface. The customized surgical guide 10 may be placed on an internal organ surface that is not exposed to the outside. To this end, the customized surgical guide 10 is made of a material that can be deformed in shape and is inserted to a specific body portion inside the body using the laparoscope while the guide is folded or wound.

Further, in another embodiment, the guide tube 100 may be fitted with the medical instrument when a distal end of the medical instrument reaches the target point 40. This allows the medical staff to recognize that the medical instrument has reached the target point 40. For example, a body of the guide tube 100 may be formed with a first diameter that allows only the needle to enter thereto, while the distal end of the guide tube 100 has a second diameter that conforms to the syringe tip. As the syringe tip is fitted in the second diameter portion of the guide tube 100 and no longer enters the body of the guide tube 100 having the first diameter. Thus, the medical staff may recognize that the target point 40 has been reached by the medical instrument. Further, when a medical instrument must apply stimulation, for example, electrical stimulation to the target point 40 for a duration longer than or equal to a specific time, the fitting between the guide tube 100 and the medical instrument maintains a state in which the medical instrument reaches the target point 40 and is fixed thereto.

Figure 4:
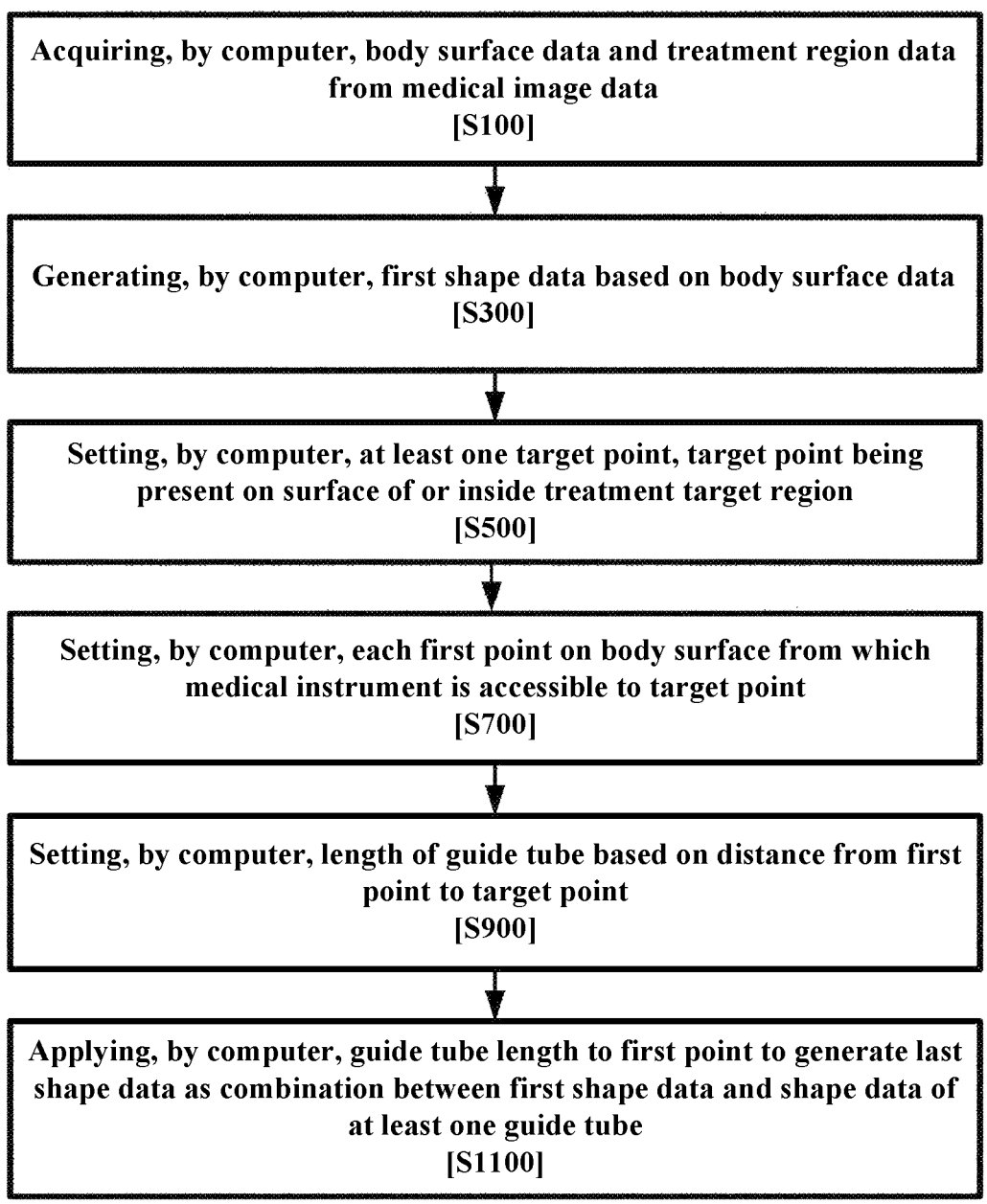
FIG. 4 is a flowchart of a customized surgical guide producing method according to one embodiment of the inventive concept.

FIG. 4 is a flowchart of a producing method of a customized surgical guide 10 according to one embodiment of the inventive concept.

Referring to FIG. 4, a producing method of a customized surgical guide 10 according to one embodiment of the inventive concept may include operation S100 in which a computer acquires body surface data and treatment region data from medical image data; first shape data generating operation S300 in which the first shape data is generated based on the body surface data by the computer, wherein the first shape data is data corresponding to a shape of the body portion cover 200; target point setting operation S500 in which at least one target point 40 is set by the computer, wherein the target point 40 is a point corresponding to the interior or surface of the treatment target region 20; operation S700 in which each first point on the body surface is set by the computer, wherein the medical instrument is accessible from the first point to the target point 40; operation S900 in which a length of the guide tube 100 is set by the computer based on a distance from the first point to the target point 40; and operation S1100 in which last shape data is generated by the computer by applying the length of the guide tube 100 to the first point, wherein the last shape data include a combination of shape data of at least one guide tube 100 and the first shape data. Hereinafter, a detailed description of each operation will be described.

The computer acquires body surface data and treatment region data from medical image data (S100). That is, the computer obtains the medical image data of the specific patient (for example, the MR image of the patient), and obtains, from the medical image data, the body surface data for forming the body portion cover 200 and the treatment region data corresponding to the treatment target region 20. Specifically, when the treatment target region 20 is a tumor, the computer extracts the tumor region from the medical image data.

The computer produces the first shape data based on the body surface data (S300: first shape data generating operation). The first shape data is data corresponding to the shape of the body portion cover 200. That is, the computer performs 3D modeling into the shape corresponding to the patient's affected surface. Thus, the customized surgical guide 10 having the body portion cover 200 that fits in the body portion of the patient may be manufactured.

Further, the computer sets, as the reference point 300, a point on the first shape data corresponding to a specific point on the body surface data. For example, when the body part to be treated (that is, the affected portion) is the breast, the computer forms a nipple hole 300 based on the nipple position on the body surface data. Thus, the computer may use the nipple hole 300 as a reference when positioning the customized surgical guide 10 on the body portion surface.

Figure 7:
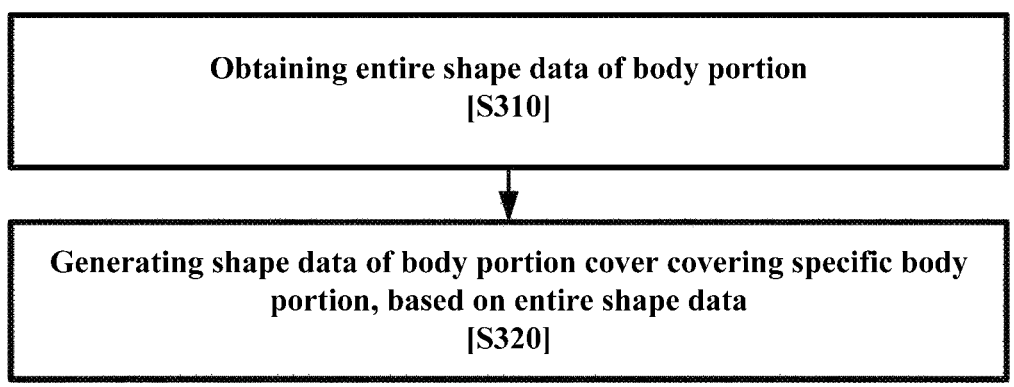
FIG. 7 is a flowchart illustrating a process of producing a body portion cover shape covering an entire body portion according to one embodiment of the inventive concept.

Further, in another embodiment, as in FIG. 7, the first shape data generating operation S300 includes operation S310 for obtaining the entire shape data of the body portion; and operation S320 for producing a shape of the body portion cover 200 covering the specific body portion based on the entire shape data. When the body portion has a shape changing according to the posture of the patient, for example, the body portion is a breast, the body portion cover should be formed to cover the entire body portion, and thus to deform and retain the body portion into and as a shape obtained at imaging of the medical image data, thereby to perform precise surgery using the customized surgical guide 10 as produced based on the medical image data. Thus, the computer acquires the entire shape of the body portion from the medical image data, and then models the body portion cover 200 into a shape covering the entire body portion.

For example, an MR imaging of the breast of a breast cancer patient is performed while the patient lies down at a state in which her face faces downwardly, whereas a breast cancer tumor removal surgery is performed while the patient lies down at a state in which her face faces upwardly. Because the shape of the breast changes due to the difference between the posture in the MR image and the posture in the surgery, the tumor position inside the breast may change. Thus, to accurately mark the tumor region inside the body via dying, the breast shape should be fixed and maintained to and as the breast shape obtained at the imaging of the medical image data during surgery. Therefore, the computer models the cover into the shape covering the entire breast, and produces the cover via injection. Then, the body portion cover 200 is placed on the breast and fixes and maintains the breast shape into that obtained at the imaging of the medical image data during surgery.

The computer sets at least one target point 40 (S500: target point setting operation). The target point 40 is the point corresponding to the interior or surface of the treatment target region 20. Specifically, the computer models the treatment target region 20 (that is, the to-be-removed region) based on the calculated target region (for example, the tumor region) with considering the error range. The computer then extracts at least one point in and on the treatment target region 2 as the target point 40.

In one embodiment, when the medical instrument is a syringe with a specific needle length, the target point 40 is set to the specific point on the surface of the treatment target region 20. That is, the target point 40 is the point on a boundary face defining a tissue to be removed via surgical surgery (that is, the tumor tissue).

Further, in another embodiment, when the medical instrument is a tool that performs treatment while a treatment range is set to a specific range around a point of a specific depth which the medical instrument reaches, the target point 40 is a specific point within the treatment target region 20. In the target point setting operation S500, the computer sets at least one target point 40 to define at least one treatment region covering the treatment target region 20. That is, the computer extracts a plurality of a specific medical instrument-based treatment ranges capable of covering the treatment target region 20 and extract multiple target points 40 defining the treatment ranges respectively which the medical instrument should reach.

The computer sets each first point on the body surface, wherein the medical instrument is accessible from the first point to the target point 40 (S700: first point set operation). For example, when the treatment target region 20 is a tumor region, the computer determines the position (that is, the three-dimensional position) on the body portion surface from which the needle may be injected toward a boundary of the tumor region.

Further, when the target point 40 is set to a point in the boundary between the treatment target region 20 and the normal tissue region, the computer sets a first point from which the medical instrument reaches the target point 40 without passing through the treatment target region 20. For example, when the treatment target region 20 is a tumor region, and when a medical instrument (such as a syringe needle) is inserted from the skin surface through the tumor region to reach the target point 40, the tumor region is damaged, such that cancer cells may be transferred to other body portions. Thus, the computer extracts the first point from which the medical instrument reaches the target point 40 without penetrating the treatment target region 20. To this end, when the target point 40 is located deeply within the body in the treatment target region 20, the computer sets the first point from which the medical instrument is accessible to the target point 40 in a lateral direction.

Further, the computer sets an orientation angle of the guide tube 100 according to the position of the first point set in association with the target point 40. For example, when the medical instrument has a straight line shape, the guide tube 100 is oriented in a direction of an extension of a straight line connecting the target point 40 and the first point. Thus, when the medical staff merely inserts the medical instrument into the guide tube 100, the medical instrument may reach the target point 40.

The computer sets the length of the guide tube 100 based on the distance from the first point to the target point 40 (S900: guide tube 100 length setting operation). The computer forms the guide tube 100 having a length such that a depth at which the medical instrument can be inserted into the body is limited to a set depth from the first point to the target point 40. For example, when the medical instrument is a syringe with a needle, the guide tube 100 is formed such that the needle is inserted into the guide tube 100 sand then the syringe is stopped by the guide tube 100 so that the needle can only enter the body by the specific depth. That is, when the length of the needle is A, and the length of the guide tube 100 is B, the needle enters the body only as long as the length corresponding to "A-B" as the syringe is stopped by the guide tube 100. Therefore, the computer sets the length of the guide tube 100 to a value calculated based on the length of the medical instrument and the distance between the target point 40 and the first point (that is, to the difference between the length of the medical instrument and the distance between the target point 40 and the first point).

The computer applies the length of the guide tube 100 to the first point to generate the last shape data as combination of shape data of at least one guide tube 100 with the first shape data (S1100: last shape data generating operation). That is, the computer generates the last shape data as the combination between the shape data of at least one guide tube 100 and the shape data of the body portion cover 200. The last shape data indicates that the guide tube 100 having a specific length and orientation is coupled to the body portion cover 200 at a specific position thereof. In other words, the computer adjusts and models the length of each of the columns of the guide tubes 100 so that the needle can reach the boundary of the tumor region accurately when the needle is inserted through each of the guide tubes.

The guide tube 100 of the customized surgical guide 10 as thus-formed performs various roles. In one embodiment, when the medical instrument is a syringe with a specific needle length, the guide tube 100 serves to assist in producing the dye column 30 in the body when the syringe supplies a dye into the body while the syringe is removed away from the target point after the syringe needle reaches the target point 40. Further, in another embodiment, the guide tube 100 plays a role in raising the accuracy of the surgery by allowing the medical instrument to reach precisely the target point 40 to be treated based on the surgery plan.

Figure 5:
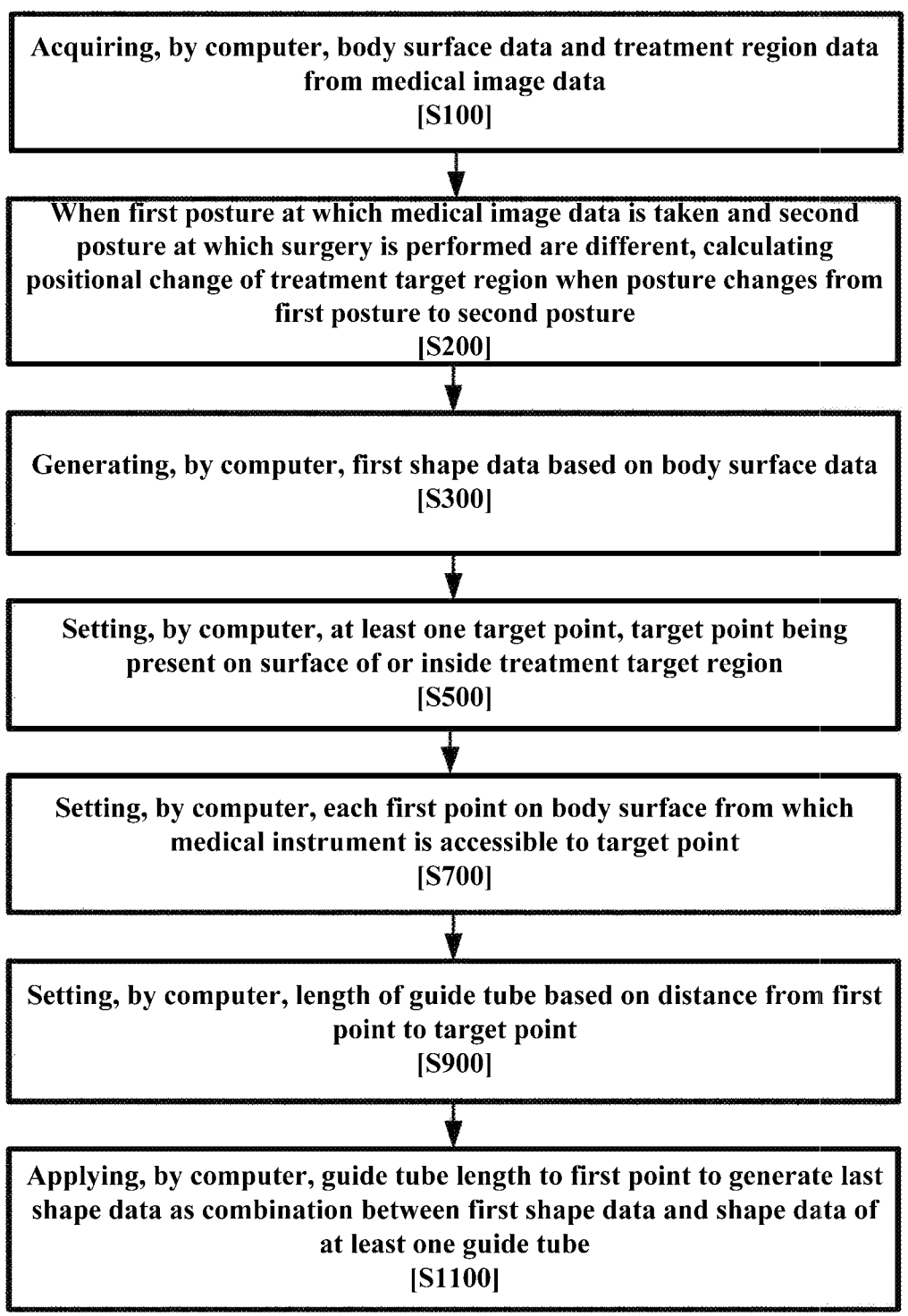
FIG. 5 is a flowchart of a customized surgical guide producing method further including calculating a position change of a treatment target region in a second posture using first posture-based medical image data, according to one embodiment of the inventive concept.

Further, in another embodiment, as shown in FIG. 5, when a first posture of the patient at which the medical image data is taken is different from a second posture of the patient at which surgery is performed, the method further includes operation S200 for calculating the positional change of the treatment target region 20 when the posture changes from the first posture to the second posture. When the medical image data is taken at a posture at which surgery is performed, the customized surgical guide 10 may be modelled based on the medical image data. However, there may be cases where a posture taken for imaging a medical image and a posture taken for surgery are different. In this case, in order to produce the customized surgical guide 10 corresponding to the second posture taken at the time of surgery, that is, in order to produce a customized surgical guide 10 that corresponds to the second posture for the surgery based on the medical image data taken at the first posture, the computer calculates the positional change of the treatment target region 20 when the posture of the body portion of the patient changes from the first posture to the second posture.

For example, among the body portions, the breast changes the shape thereof flexibly according to the posture of the patient. The MR image is taken at the first posture in which the patient lies down with her face facing downwardly, whereas the surgery is performed at the second posture in which the patient lies down with her face facing upwardly. Therefore, the breast shape may vary between the MR image capture and the surgery. As the breast shape changes, a position of the tumor tissue in the breast in the three-dimensional space may vary. Therefore, the computer identifies the breast shape in the second posture based on the size of the breast, and the breast shape in the first posture, and calculates the position of the tumor in the breast shape in the second posture (that is, calculates the position of the treatment target region 20).

Further, when a medical image is taken at the first posture and then the customized surgical guide 10 corresponding to the second posture is modeled, the target point setting operation S500, the first point setting operation S700, and the guide tube length setting operation S900 may be performed based on the changed position of the treatment target region 20.

In yet another embodiment, the first shape data generating operation S300 calculates the shape of the body portion in the second posture based on the medical image data obtained in the first posture, and models the shape data of the body portion cover 200 (that is, the first shape data) based on the calculated shape data.

Further, in another embodiment of the inventive concept, where the medical instrument is curved at a specific curvature, the computer produces the guide tube 100 at the same curvature as that of the medical instrument. A straight line shaped medical instrument may have difficulty in reaching the target point 40 in the body. In this case, the curved medical instrument may be used. In order to insert the curved medical instrument having a specific curvature through the customized surgical guide 10 into the body, the guide tube 100 must be made at the same curvature as that of the medical instrument and be smoothly inserted. Thus, on the medical plan, the medical instrument may reach the accurate target point 40.

Further, in order to model the guide tube 100 into which a bent curved medical instrument is inserted, the first point setting operation 700 extracts the first point from which the medical instrument reaches the target point 40 while moving inside the body along a curved path. That is, the computer extracts not a first point from which the medical instrument reaches the target point 40 when moving along a straight-line path, but a first point from which the medical instrument reaches the target point 40 when moving along a specific curvature-based path.

Further, the last shape data generating operation S1100 generates the curvature of the guide tube 100 equal to the curvature of the medical instrument. The last shape data generating operation S1100 calculate the curve length of the guide tube 100 by subtracting, from the medical instrument length, the distance by which the medical instrument should travel along the curved path in the body.

Figure 6:
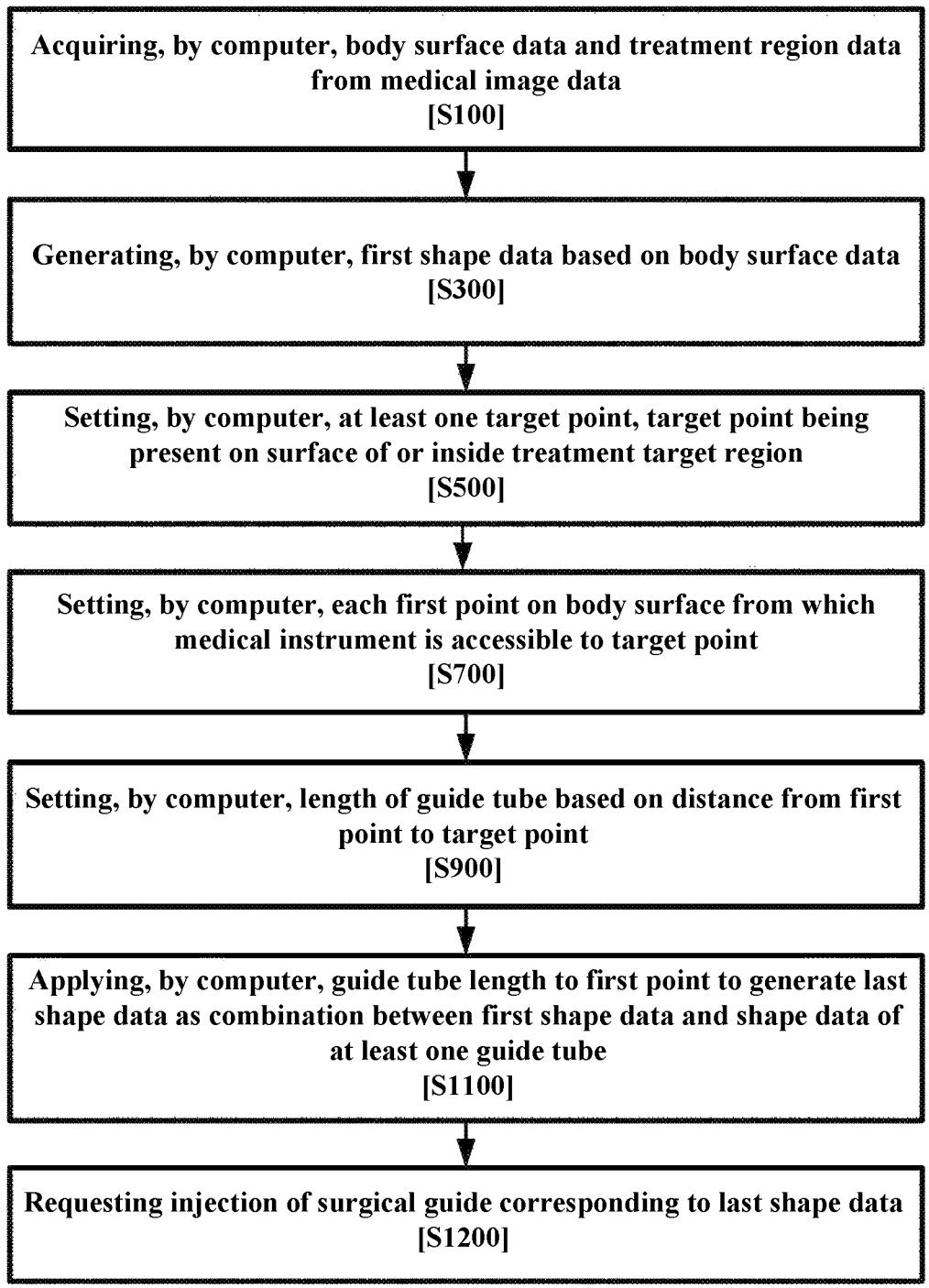
FIG. 6 is a flowchart of a customized surgical guide producing method further including requesting injection based on last shape data according to one embodiment of the inventive concept.

Further, as shown in FIG. 6, another embodiment of the inventive concept further includes operation S1200 for requesting injection of the surgical guide corresponding to the last shape data. That is, the computer requests injection of the guide corresponding to the modeled last shape data to a 3D injection device, that is, a 3D printer.

The above-described method of producing the customized surgical guide 10 according to one embodiment of the inventive concept as described may be implemented using a program (or application) to be executed in combination with a computer as hardware, which may be stored in a medium.

The above-mentioned program may include codes encoded in a computer language such as C, C++, JAVA, or machine language which the computer's processor (CPU) can read via a device interface of the computer. Thus, when the computer reads and executes the program, the program may perform the method. These codes may include functional codes related to functions that define necessary functions to execute the method, or may include executable procedure-related control codes necessary for the processor of the computer to execute the functions in accordance with a predetermined procedure. Further, these codes may further include memory reference-related code that indicates where additional information or media needed for the execution of the functions by the computer's processor is addressed to any location (address) in the computer's internal or external memory. Further, when the computer's processor needs to communicate with any other computer or server at a remote location to execute the functions, the codes may further include communication related codes indicating, for example, how to communicate with any other computer or server remotely using a communication module of the computer, and what information or media as transmitted or received therebetween during communication.

The storage medium is not a medium for storing data for a short time such as a register, a cache, a memory, etc., but means a medium that semi-permanently stores data and is capable of being read by a device. Specifically, examples of the storage medium include, but are not limited to, ROM, RAM, CD-ROM, magnetic tape, floppy disk, optical data storage, and the like. That is, the program may be stored on various recording media on various servers that the computer can access, or on various recording media on the user's computer. Further, the medium may store therein computer readable codes as distributed over a networked computer system and as read by the computer in a distributed manner.

According to the inventive concept as defined above, following various effects may be realized.

First, using the customized surgical guide 10 that assists in performing patient-customized surgery may allow optimal surgery for the patient. For example, when a to-be-removed lesion (for example, tumor) within the affected portion should be removed, the patient-customized surgical guide 10 is used to produce at least one dye column 30 in the body portion. The dye column may be used to allow the medical staff to visually check the to-be-removed region during surgery. Thus, the medical staff may remove a minimal tissue via two-or three-dimensional marking using the dye column 30.

Second, since the guide tube 100 is produced by calculating a depth to the target point 40 based on the medical image data, the medical staff may perform the surgery without paying attention to the depth of insertion of the medical instrument, (for example, syringe). In other words, when the medical instrument is fully inserted into the guide tube 100 of the customized surgery guide, the medical instrument reaches the target point 40, so that the surgery can be easily performed.

Third, the body portion cover 200 is shaped to conform to the body portion shape, and the body portion cover 200 defines a position of the guide tube such that the medical instrument accurately reaches the target point 40 within the body portion. This prevents treatment from being performed on a wrong target point 40 or prevents erroneously marking in the body portion.

Fourth, even when there is a difference between a posture of the patient at which the medical image data is obtained and a posture of the patient at which the surgery is performed, the customized surgical guide 10 may allow the medical instrument to accurately reach the target point.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A customized surgical guide comprising:
   a plurality of guide tubes through which medical instruments are insertable; and a body portion cover configured to cover a surface of a breast of a patient,
wherein the body portion cover is coupled to the plurality of guide tubes, wherein the body portion cover has holes through which the medical instruments pass,
wherein the medical instruments are configured to pass through the plurality of guide tubes and then through the holes toward the breast,
wherein the body portion cover is shaped to conform to the surface of the breast,
wherein the body portion cover defines positions of the plurality of guide tubes such that the medical instruments reach target points within the breast,
wherein a respective guide tube of the plurality of guide tubes has a larger inner diameter than an outer diameter of a respective medical instrument of the medical instruments,
wherein the respective guide tube has a length sized such that an insertable depth of the respective medical instrument into the body is limited to a set depth from a respective first point of first points to a respective target point of the target points,
wherein the first points are present on the surface of the breast, at which the plurality of guide tubes are configured to be located,
wherein the target points are present on a surface of or inside a treatment target region, or are spaced by specific distances from the treatment target region.

2. The customized surgical guide of claim 1, wherein the respective the medical instrument is a syringe including a needle having a specific needle length, and the respective guide tube is formed so that the needle of the syringe reaches the respective target point,
wherein the respective target point is a starting point of a dye column, and
wherein the dye column is configured to formed by a dye being supplied by the syringe during the syringe that is fully inserted into the guide tube is removing away from the respective target point through the respective guide tube.

3. The customized surgical guide of claim 1, wherein the respective medical instrument is configured to perform treatment on a treatment range defined as a specific range from a specific point which the inserted respective medical instrument reaches, the respective target point is at least one specific point located within the treatment target region, wherein the at least one specific point defines at least one treatment range covering the treatment target region, wherein a number of the guide tubes is equal to a number of the target points, wherein the respective guide tube is formed on the respective first point of the body portion cover and extends in a direction from the respective first point toward the respective target point.

4. The customized surgical guide of claim 1, wherein the body portion cover is formed to conform to body surface acquired based on medical image data, and wherein the respective guide tube has a length set based on a respective distance on the medical image data from the respective first point on the body surface to the respective target point that the respective medical instrument is configured to reach.

5. The customized surgical guide of claim 1, wherein the body portion cover is configured to fix a shape of the breast into a specific shape that is measured when body surface data and treatment region data are acquired by a computer from medical image data.

6. The customized surgical guide of claim 1, wherein when a distal end of the respective medical instrument reaches the respective target point, the respective guide tube is fitted with the respective medical instrument.

7. The customized surgical guide of claim 1, wherein the body portion cover comprises a nipple hole having the same size as a nipple of the breast at a position corresponding to the nipple of the breast.

8. The customized surgical guide of claim 1, wherein the target points are points on a three-dimensional space of the treatment target region having a three-dimensional breast shape.

9. A method of producing a customized surgical guide, the guide including a plurality of guide tubes through which medical instruments are inserted, and a body portion cover contacting a surface of a breast of a patient, the method comprising:
acquiring, by a computer, body surface data and treatment region data from medical image data;
generating, by the computer, first shape data based on the body surface data, the first shape data defining a shape of the body portion cover;
setting, by the computer, target points, which are present on a surface of or inside a treatment target region;
setting, by the computer, a respective first point of first points, on the body surface from which the medical instruments are accessible to a respective target point of the target points;
setting, by the computer, a respective length of a respective guide tube of the plurality of guide tubes based on a respective distance from the respective first point to the respective target point; and
applying, by the computer, the respective guide tube length to the respective first point to generate last shape data as a combination between the first shape data and shape data of the respective guide tube.

10. The method of claim 9, wherein the respective medical instrument is a syringe including a needle having a specific needle length, and the respective guide tube is formed so that the needle of the syringe reaches to the respective target point,
wherein the respective target point is a starting point of a dye column, and
wherein the dye column is configured to formed by a dye being supplied by the syringe during the syringe that is fully inserted into the respective guide tube is removing away from the respective target point through the respective guide tube.

11. The method of claim 10, wherein the setting of the respective first point includes setting the respective first point from which the respective medical instrument reaches the respective target point without passing through the treatment target region.

12. The method of claim 9, wherein the respective medical instrument is configured to perform treatment on a treatment range defined as a specific range from a specific point which the respective inserted medical instrument reaches, the respective target point is at least one specific point located within the treatment target region, wherein the setting of the respective target point includes setting the respective target point to define at least one treatment range covering the treatment target region.

13. The method of claim 9, wherein the generating of the first shape data includes:
obtaining entire shape data of the breast; and
generating shape data of the body portion cover covering the breast based on the entire shape data,
wherein the body portion cover covers the breast and fixes a shape of the breast into a specific shape.

14. The method of claim 9, wherein a first posture of a patient at which the medical image data is taken and a second posture of the patient at which surgery is performed are different, the method further comprises:
    calculating a positional change of the treatment target region when a posture of the patient changes from the first posture to the second posture,
    wherein the setting of the respective target point, the setting of the respective first point, and the setting of the respective length of the respective guide tube are performed based on the changed position of the treatment target region.

15. The method of claim 9, wherein the respective medical instrument is curved at a specific curvature, the setting of the respective first point includes setting the respective first point from which the respective medical instrument reaches the respective target point while moving along a curved path having the specific curvature within the body,
    wherein the generating of the last shape data includes generating curvature data of the guide tube equal to the curvature of the respective medical instrument.

16. A customized surgical guide producing program stored in a medium for carrying out the method of claim 9 in combination with a computer as hardware.

17. The method of claim 9, wherein the first data comprises information of the nipple of the breast to define a size and a position of a nipple hole of the body portion cover.

18. The method of claim 9, wherein the target points are points on a three-dimensional space of the treatment target region having a three-dimensional breast shape.

\* \* \* \* \*